US008087783B2

(12) United States Patent
Peyman

(10) Patent No.: US 8,087,783 B2
(45) Date of Patent: Jan. 3, 2012

(54) OCULAR CENTRATION OF VISUAL AXIS AND EVALUATION OF RETINAL FUNCTION

(76) Inventor: Gholam A. Peyman, Sun City, AZ (US)

( * ) Notice: Subject to any disclaimer, the term of this patent is extended or adjusted under 35 U.S.C. 154(b) by 6 days.

(21) Appl. No.: 12/765,578

(22) Filed: Apr. 22, 2010

(65) Prior Publication Data

US 2010/0201947 A1  Aug. 12, 2010

Related U.S. Application Data

(63) Continuation of application No. 12/401,966, filed on Mar. 11, 2009, now Pat. No. 7,731,364.

(60) Provisional application No. 61/035,549, filed on Mar. 11, 2008, provisional application No. 61/035,555, filed on Mar. 11, 2008, provisional application No. 61/082,252, filed on Jul. 21, 2008, provisional application No. 61/038,808, filed on Mar. 24, 2008, provisional application No. 61/046,930, filed on Apr. 22, 2008, provisional application No. 61/053,077, filed on May 14, 2008.

(51) Int. Cl.
*A61B 3/00* (2006.01)
(52) U.S. Cl. ........................................... 351/246
(58) Field of Classification Search .................... 351/246
See application file for complete search history.

(56) References Cited

U.S. PATENT DOCUMENTS

| 4,545,658 | A | * | 10/1985 | Weiss | 351/222 |
| 5,752,967 | A | | 5/1998 | Kritzinger et al. | |
| 6,176,581 | B1 | | 1/2001 | Newsome | |
| 6,533,419 | B1 | | 3/2003 | Newsome | |
| 6,863,399 | B1 | | 3/2005 | Newsome | |
| 2004/0087843 | A1 | * | 5/2004 | Rice et al. | 600/319 |
| 2005/0010091 | A1 | * | 1/2005 | Woods et al. | 600/316 |
| 2006/0200013 | A1 | * | 9/2006 | Smith et al. | 600/319 |
| 2007/0121071 | A1 | * | 5/2007 | Jackson et al. | 351/246 |

OTHER PUBLICATIONS

Shelley, et al., Cone Degeneration in Aging and Age-Related Macular Degeneration, Arch Ophthalmol vol. 127, (No. 4) (Apr. 2009).
Newsome, David A. and Negreiro, Manny, Reproducible Measurement of Mascular Light Flash Recovery Time Using a Novel Device Can Indicate the Presence and Worsening of Macular Diseases, Current Eye Research, vol. 34, (2009) pp. 162-170.
Montes-Mico, et al, Intraocular lens centration and stability: efficacy of current technique and technology, Curr Opin Ophthalmol, vol. 20, (2009) pp. 33-36.

* cited by examiner

*Primary Examiner* — James Greece
(74) *Attorney, Agent, or Firm* — Thompson Hine LLP

(57) ABSTRACT

A method and device to assess centration of a visual axis, evaluate retinal function, foveal function, and/or visual field.

7 Claims, 14 Drawing Sheets

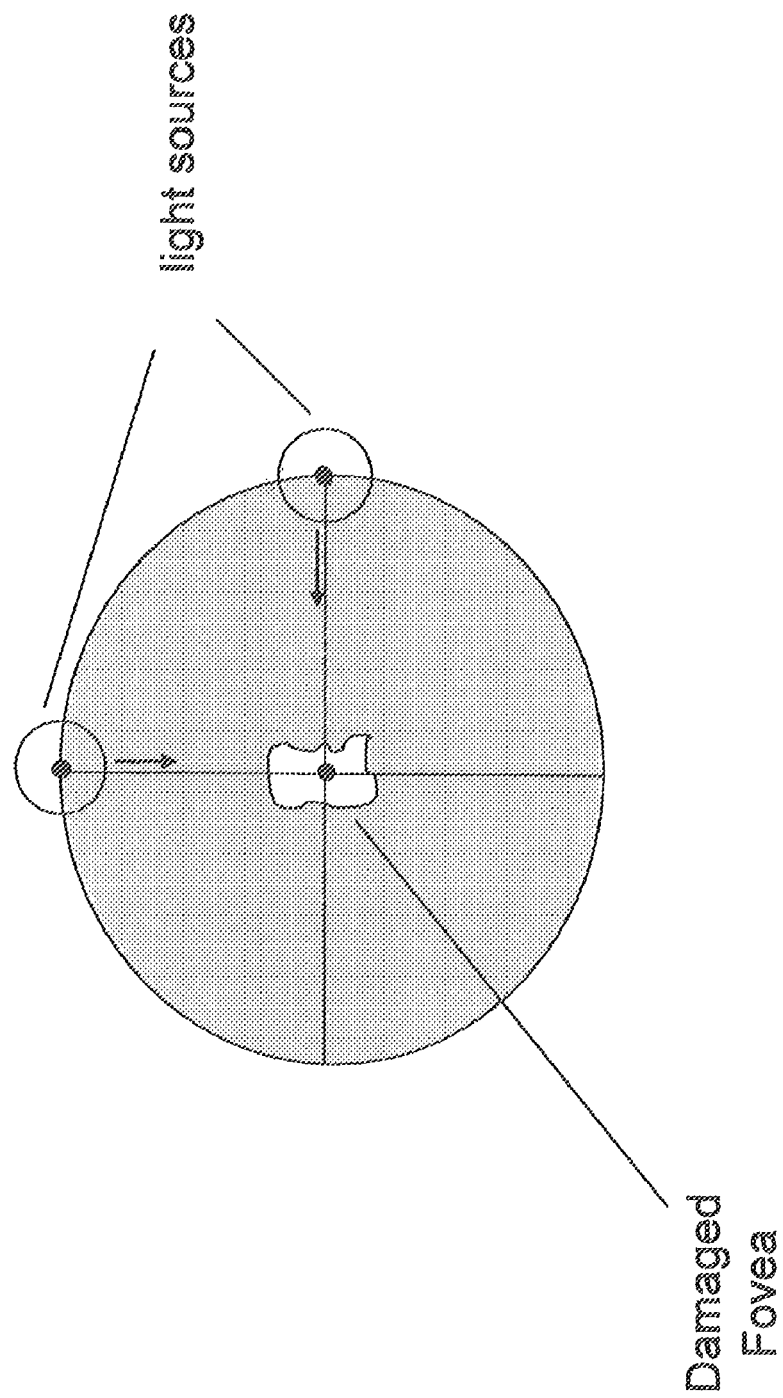

OCULAR CENTRATION OF VISUAL AXIS AND EVALUATION OF RETINAL FUNCTION

RELATED APPLICATIONS

This application is a continuation of U.S. patent application Ser. No. 12/401,966, filed Mar. 11, 2009 now U.S. Pat. No. 7,731,364, which claims priority from U.S. Application Ser. Nos. 61/035,549 filed on Mar. 11, 2008; 61/035,555 filed on Mar. 11, 2008; 61/082,252 filed on Jul. 21, 2008; 61/038,808 filed on Mar. 24, 2008; 61/046,930 filed on Apr. 22, 2008 and 61/053,077 filed on May 14, 2008, the entire text of which is expressly incorporated by reference herein.

BRIEF DESCRIPTION OF THE DRAWINGS

FIG. 8 depicts photoreceptor fatigue and exhausted photoreceptor recovery.

One embodiment is a method to assess and maintain centration of a visual axis. The method comprises having a patient focus or fixate on a circular image throughout a procedure. The procedure may be a surgical procedure or another type of procedure. The procedure is then performed in view of, i.e., is performed with, centration of the visual axis assessed and maintained throughout the procedure by the patent's focus on the image. In one embodiment, the procedure is in situ keratomileusis (LASIK), photorefractive keratectomy (PRK), or laser assisted sub-epithelial keratomileusis (LASEK). In one embodiment the image is that of FIG. 1 or FIG. 2.

One embodiment is a method to self-assess ocular centration of a target in a visual axis. The method comprises having a patient focus on a circular image between a target and an eye, the circular image on a lens external to the eye, the center of the circular image defining a visual axis for the patient looking through the lens at a target. The patient self-aligns the target in the visual axis to self-assess ocular centration of the target by the extent of self-aligning of the target required. The circular image may be on a pair of glasses (spectacles) worn by an individual.

Figure 1:
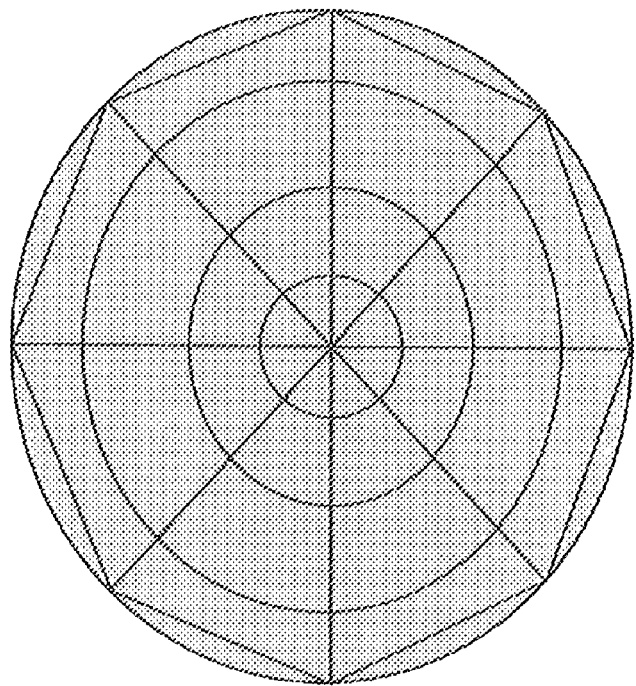
FIG. 1 shows one embodiment of an image that defines a circle having an area sufficient to identify a focus on its center.
Figure 1A:
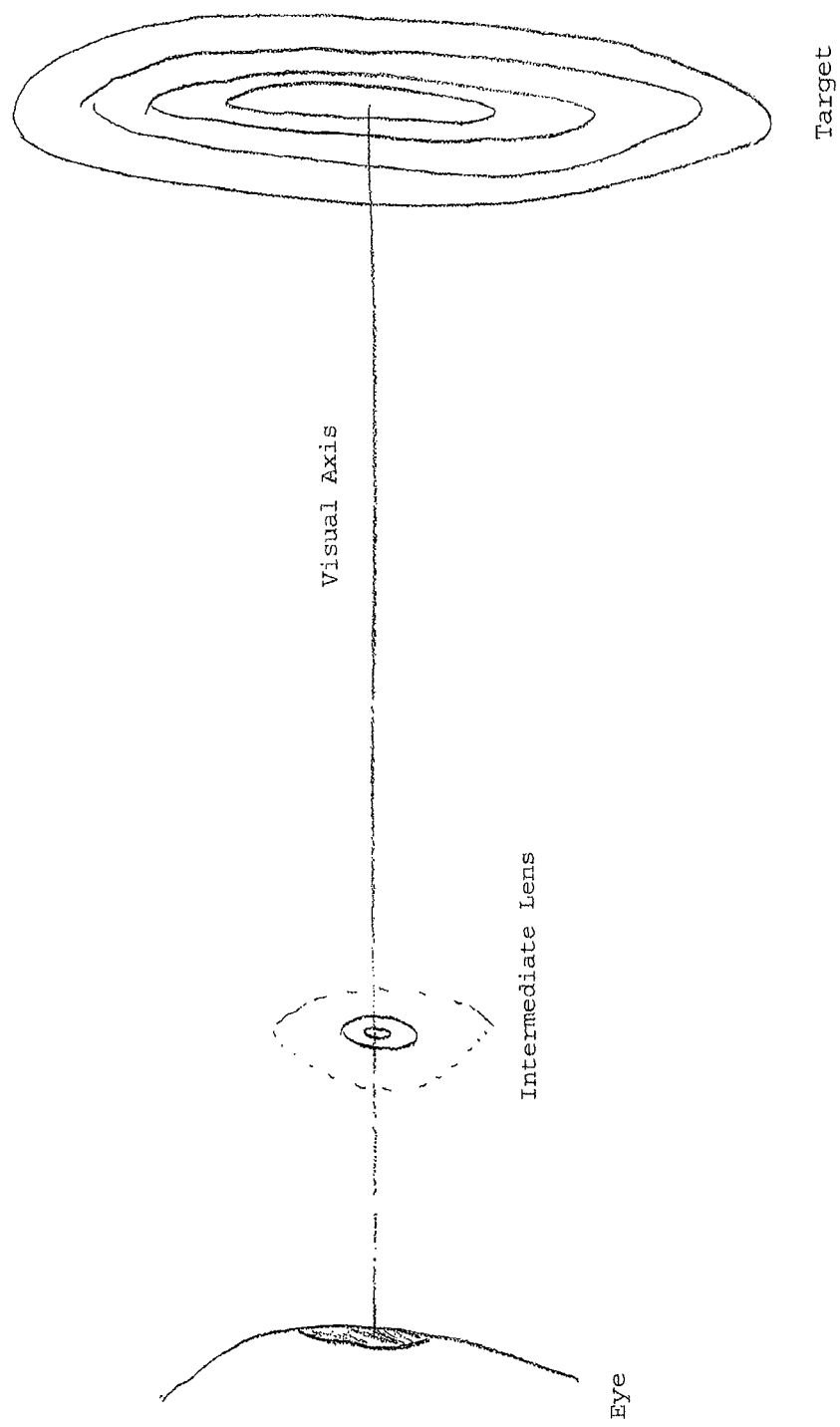
FIG. 1A show an embodiment of an image projected or marked on a lens in the visual pathway.

In one embodiment, the image is projected or marked on a lens in the visual pathway, e.g., FIG. 1A. The lens may be an intraocular lens inserted in the eye, or the lens may be external to the eye (e.g., glasses worn by a user), or the lens may be on a device such as a scope. The image permits centration of all optical elements. In this embodiment no treatment is desired, but accurate visual alignment is desired. In one embodiment, the individual is participating in a sport or activity requiring visual alignment, for example, photography, hunting, golfing, billiards, archery, darts, etc., and can use the image to center his/her visual axis in alignment with an object such as a subject, target, ball, etc. In one embodiment, the individual is using a weapon requiring visual alignment (e.g., rifle, gun, etc.) and can center his/her visual axis in alignment with a human or non-human target. In this embodiment, use may be in simulated combat for training purposes, in actual combat for military purposes, in a national security situation, for example, a sharpshooter sighting a hijacker, a paratrooper attempting to land at a particular target, etc. The image may be placed on devices including, but not limited to, glasses, binoculars, telescopes, weapon scopes, surveying equipment, computer-controlled optics (e.g., surgical instrument, space exploration equipment (e.g., Mars Rovers, Mars Polar Lander)), drills, underwater cameras, etc. In one embodiment, the individual has an occupation requiring visual alignment, such as a soldier, craftsperson, surgeon, technician, astronaut, photographer, etc. It may assist individuals in the military, participating in activities, participating in sports, etc., to recognize landscape relief such as hills, curves, troughs, etc.

One embodiment is a lens comprising an image of at least one circle, the center of the circle viewable by an individual wearing the lens, the center defining a visual axis for the individual looking through the lens at a target and aligning the target in the visual axis of the individual. The lens may be a glass, video screen, a single lens, multiple lenses supported by a frame, or computer controlled optics. The lens may be in or on spectacles, binoculars, a telescope, a weapon scope, surveying equipment, or computer-controlled optics.

One embodiment is a method to assess centration of a visual axis in a patient having a retinal disease. The method comprises having a patient with a retinal disease focus on a circular image and mapping the patient's visual axis, and thereafter periodically repeating the method to compare the visual axis of the patient over time to assess disease progression. The retinal disease may be age-related macular degeneration, retinitis pigmentosa, diabetic retinopathy, glaucoma, or optic nerve disease.

One embodiment is a device for displaying an image to assess and maintain a visual axis. The device comprises a programmable image of a circle having an area sufficient for a human eye to locate a center of the circle, and software to display a visual axis to a user when the human is directed to look at the center of the circle. The whole image or part of the image is selectively illuminated by a single light or a moving light.

One embodiment is a method to assess and maintain ocular centration of a visual axis. The method comprises having a patient focus on a circular image throughout a corneal inlay or onlay. The corneal inlay or onlay is performed in view of centration of the visual axis assessed and maintained throughout the procedure by the individual's focus on the image. The image may be that of FIG. 1 or FIG. 2.

One embodiment is a method to assess recovery of a compromised retinal area in a patient. The method comprises moving a light source at a predetermined speed laterally across the fovea, then determining a time interval between a patient seeing a continuous line and a discontinuous line, and then comparing the time interval to a known time interval to assess the patient's extent of recovery. In one embodiment, the patient's time interval is compared to the time interval in a patient with an uncompromised retina to assess recovery of the compromised retina. In one embodiment, the patient's time interval is compared to a previous time interval measured in the same patient under substantially the same conditions to assess extent of recovery of the compromised retina. The area is specifically located by a centration method. The patient indicates seeing an afterimage from the light source. If the patient indicates seeing at least two afterimages, this indicates at least two compromised areas of the retina.

One embodiment is a method to assess recovery of a compromised retinal area in a patient. The method comprises moving a light source at a predetermined speed across the retinal area, determining a time interval between a patient seeing a continuous line and a discontinuous line, and comparing the time interval to a known time interval to assess the patient's extent of recovery. The retinal area may be a peripheral retina area, a central retina area, and/or a fovea. The patient's time interval is compared to the time interval in a patient with an uncompromised retina to assess recovery of the compromised retina. The patient's time interval is compared to a previous time interval measured in the patient under substantially the same conditions to assess extent of recovery of the compromised retina. The area is specifically located by centration projected on the retina. Centration may be projected by an illumination device, by a camera, by a patient viewing a circular image, etc. The patient indicates seeing an afterimage from the light source. If the patient indicates the presence of at least two afterimages, this indicates at least two compromised areas of the retina.

One embodiment is a method to assess recovery of rod function in a dark adapted retina. The method comprises moving a light source at a predetermined speed laterally across the fovea of a patient in a dark adapted state, determining a time interval between the patient seeing a continuous line and a discontinuous line, and comparing the time interval to a known time interval to assess the extent of rod recovery in the patient. The patient's time interval is compared to the time interval in a patient with an uncompromised retina to assess recovery of the compromised retina. The patient's time interval is compared to a previous time interval measured in the same patient under substantially the same conditions to assess extent of recovery of the compromised retina. The area is specifically located by a centration method. The patient indicates seeing an afterimage from the light source. If the patient indicates seeing the presence of at least two afterimages, this indicates at least two compromised areas of the retina.

One embodiment is a method to assess recovery of cone function in a light adapted retina. The method comprises moving a light source at a predetermined speed laterally across the fovea of a patient in a light adapted state, determining a time interval between the patient seeing a continuous line and a discontinuous line, and comparing the time interval to a known time interval to assess the extent of cone recovery in the patient. The patient's time interval is compared to the time interval in a patient with an uncompromised retina to assess recovery of the compromised retina. The patient's time interval is compared to a previous time interval measured in the same patient under substantially the same conditions to assess extent of recovery of the compromised retina. The area is specifically located by a centration method. The patient indicates seeing an afterimage from the light source. If the patient indicates seeing the presence of at least two afterimages, this indicates at least two compromised areas of the retina.

One embodiment is a method of simultaneously evaluating a visual field and retinal function in a patient. The method comprises fixating the patient's vision on a target comprising circular concentric rings, mapping the visual field and retinal function using a static or moveable light source, and recording a recovery time of at least one retinal area by stimulating the retinal area with subsequent weak pulses relative to the mapping light source until recognized by the patient. The method measures the recovery time by a second weaker light pulse, it does not require the patient to recognize a letter or number. This evaluates retinal function in the peripheral portion of the retina, independent of the patient having a reading function or ability.

Ocular Centration of Visual Axis

Optimal vision results when the incoming light rays in the visual axis are accurately centered or aligned on the fovea. The fovea, the centermost portion of the macula, is the area of the retina that is responsible for sharp vision due to its high concentration of photoreceptors.

The visual axis is the path that connects an object viewed by the eye to the fovea, and corresponds to the optical center of the cornea, lens, and retina. By accurately defining the location of the visual axis, the physician can correct refractive errors in the visual axis that lead to suboptimal vision.

Ocular surgical procedures, particularly those that involve the cornea, lens, and retina, can disrupt the visual axis. Examples of such surgical procedures include elective procedures to correct refractive errors such as laser assisted in situ keratomileusis (LASIK), photorefractive keratectomy (PRK), laser assisted sub-epithelial keratomileusis (LASEK), insertion of corneal inlays, and insertion of corneal onlays.

The physician performing such surgical procedures must precisely know the visual axis location, and must continuously monitor the visual axis location throughout the procedure. For example, during laser ablation of the cornea that occurs during PRK, or that occurs during LASIK after a corneal flap is created, the physician or the computer-guided laser must know the center of the visual axis in order to maintain the visual axis during the entire ablation process. During ocular implant and inlay procedures, one cannot assume that the center of the pupil is the center of the visual axis, because the pupil is not always an exact indicator of the visual axis, hence making the pupil an unsatisfactory centration point.

An image of at least one circle having an area sufficient to locate the center of the circle is displayed to an individual. The individual, by focusing on the center of the circle, aligns the visual axis such that the visual axis is maintained regardless of the presence of an ocular pathology decreasing vision, such as age-related macular degeneration. In one embodiment, the inventive method and device is used to assess centration of the visual axis. In one embodiment, the inventive method and device is used to maintain proper centration around the visual axis.

Figure 2:
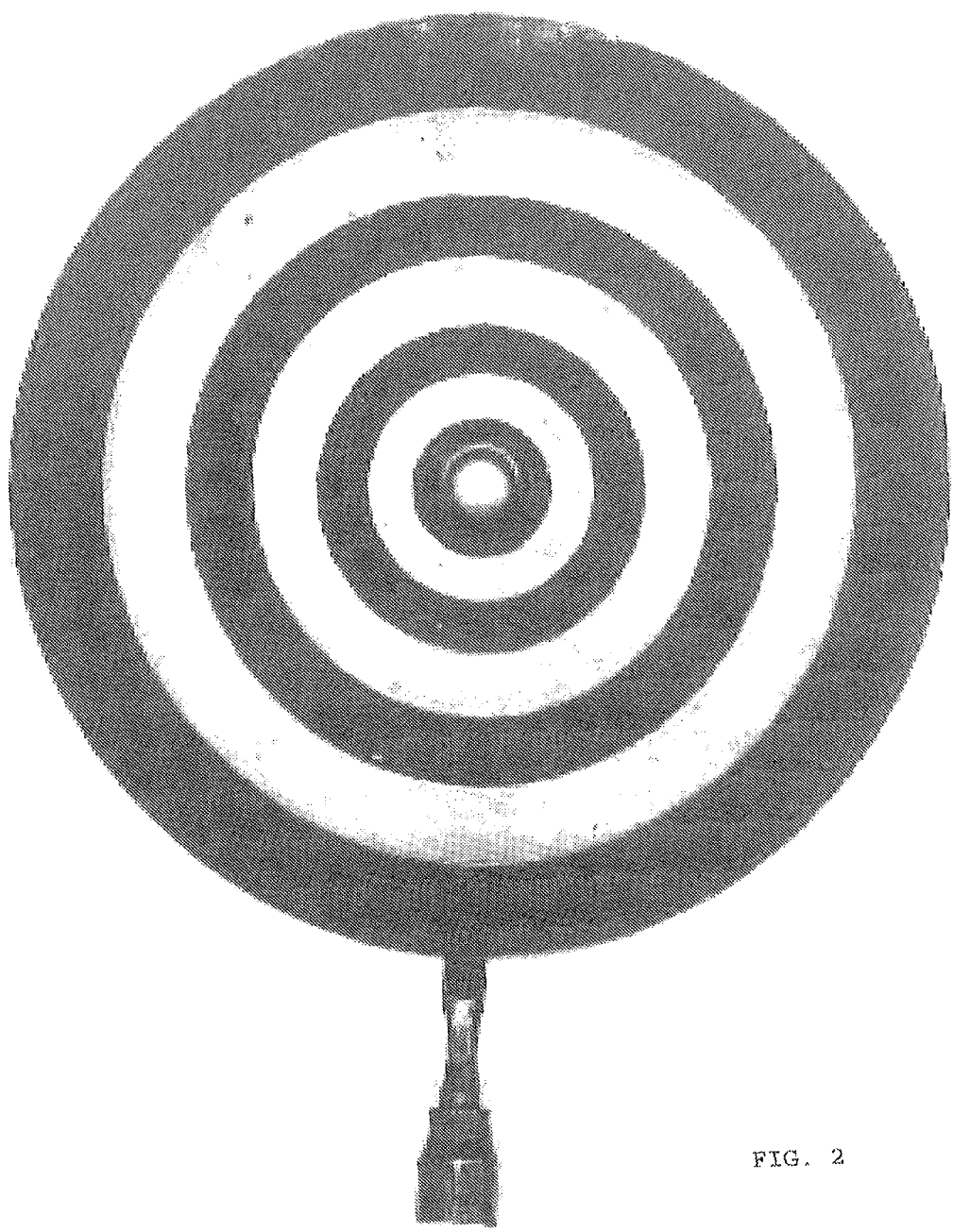
FIG. 2 shows another embodiment of an image that defines a circle having an area sufficient to identify a focus on its center.

In one embodiment, a patient is instructed to look at the center of an image that defines a circle, the circle having an area sufficient to identify a focus on its center. The circle may be, but need not be, continuous. In one embodiment, the circular image is at least two concentric circles. In one embodiment, the circular image is one circle. Examples of images are shown in FIG. 1 and FIG. 2. FIG. 1 is a series of concentric circles. FIG. 2 is a keratocope (also known as Placido's disc), a circular image of alternating black and white rings; when reflected on the cornea, it projects corneal contours that permits a physician to assess corneal surface irregularities and astigmatism, to compute corneal curvature during surgery, and to gather preoperative data in corneal topography assisted LASIK. Before Applicant's method, it had not been used to define the location of the visual axis nor to maintain centration.

When the individual looks at the center of such a circular image, the eye recognizes the pattern reflected from the image and self-focuses on the center. Such centration occurs even in individuals with a damaged fovea, such as patients with age-related macular degeneration, because the perifoveal area has a circular representation in the brain. Thus, by having the patient consistently look at the image during the entire surgical procedure, the physician, or computer-guided laser, is assured of accurate centration of the visual axis at all times. The physician, or computer-guided laser, can see the visual axis on the patterns reflected on the cornea, and thus is able to maintain centration throughout the entire procedure.

The image is displayed by a means that is not invasive and is readily tolerated by a patient. In one embodiment, the image is projected onto the cornea, the lens (if the pupil is dilated), or the retina during the surgical procedure. The innermost circle is centered around the fovea. This may occur simultaneously with the individual viewing the image. Alternatively, this may occur with the physician viewing the image projected by an instrument on the eye and simultaneously visualizing the retina by a camera. In one embodiment, the image is projected using a device containing software programmed to display and project the image. The device may permit the user to adjust the image size, brightness, intensity, etc. The software may allow measurements to be taken throughout the procedure. In one embodiment, the circles projected may be optically manipulated to become larger or smaller, as needed or desired.

In one embodiment, an image is projected using a computerized Placido disk projecting system as described by Carvalho et al., International Society for Optical Engineering, 2003. Carvalho's projecting system is attached to the objective lens of a surgical microscope, and the pattern is reflected by a 50% beam splitter attached to the microscope body. The beam splitter contains an adaptor and a CCD monochromatic high resolution camera. A frame grabber is installed on a personal computer and images are digitized at a 480×640 resolution. Algorithms based on image processing techniques are implemented for edge detection of patterns.

In one embodiment, the image is displayed as a hard copy (e.g., on paper) and is positioned within the patient's visual field. In one embodiment, the image is programmed on software and displayed on a computer screen positioned within the patient's visual field. In one embodiment, the image is displayed as lights on a circle.

Traditionally, centration is assessed by projecting a beam of light into the eye to define the location of the visual axis. However, this beam of light causes patient discomfort because the patient is instructed to stare at the beam of light for an extended time. Because the patient is rapidly blinded by staring at this beam of light, he/she has a tendency to move the eye, and hence the visual axis, away, thus changing the location of the visual axis. In addition, even a minimal cloudiness in the beam path will cause the eye to move attempting to see it.

Using the inventive method and device, the patient is not exposed to a single beam of light projected into his/her eye (fovea) so there is no discomfort. Patient movement will not occur because the image has a larger area than a single beam of light. Because the patient is instructed to attentively look at the center of circles, the patient automatically centers the fovea in line with the visual axis. The method is used to access centration even on a sub- or non-functional fovea, as occurs in patients with age-related macular degeneration.

In one embodiment to assess centration, the physician marks four areas at the limbus (the edge of the cornea where the cornea meets the sclera) using a dye or an instrument (e.g., as described in U.S. Pat. No. 5,752,967 which is incorporated by reference herein). The physician instructs the patient to attentively focus at the center of either FIG. 1 or FIG. 2. The eye recognizes the pattern reflected from the image and self-focuses on the center of the image. A digitized photograph is taken while the circles are projected on the cornea, defining the relationship between the four peripheral points to the location of the visual axis on the cornea. In one embodiment, the digitized photograph is transferred to a computer.

In one embodiment, the computer controls the center of an ablation profile performed with a laser. In one embodiment, the information is reflected back on the cornea. This indicates to the physician performing a corneal inlay procedure, after making the corneal flap, the exact location of the visual axis, now visible on the corneal bed. The physician then places the corneal inlay and verifies the borders of the inlay in relation to the visual axis using the projected image. This results in accurate centration of the inlay.

In one embodiment, a test individual (patient) self-evaluates his/her central field and potentially marks the distorted area. The central field is the area of the retina (fovea and macular area). The individual is instructed to attentively focus on an image of a continuous circle, or a series of concentric circles, on a screen, or paper, etc. The circles are positioned at a set distance from the patient, standardized by having the patient positioned with chin and forehead rests. Because the image is positioned at a defined distance from the eye, it always creates the same size image over the retina.

In one embodiment, the circles may be illuminated at various points on a given circle (e.g., if paper, the illumination points are holes at a set distance from each other with an illumination source; if digitally projected, the illumination points are electronically set while the image rotates around its axis at a given speed.

In one embodiment, the inventive method and device is used for accurate centration of a corneal inlay. For projection over the cornea to accurately place a corneal inlay, one or multiple circles are needed. These define not only the visual axis, regardless of the position of the pupil or function of the macula, but also define the potential border of an inlay or only inside the cornea. The inventive method and device eliminates decentration of the inlay or onlay, which is a potential surgical complication.

In one embodiment, the inventive method and device is used for accurate centration of an excimer laser. For projection over the cornea to guide an excimer laser over the cornea, one or multiple circles are needed. These define not only the visual axis, regardless of the position of the pupil or function of the macula and/or fovea, but also the area of excimer laser application over the cornea either on the corneal surface as in PRK, or under a corneal flap as in LASIK. The inventive method and device eliminates decentration of the laser application, which is a potential surgical complication.

In one embodiment, the inventive method and device is used for accurate centration of an intraocular lens that is fixed to the iris or inside the capsular bag, i.e., centration of a multifocal intraocular lens. Examples include centration of phakic lenses, aphakic lenses, pseudophakic lenses, spheric lenses, aspheric lenses, and others known to a person of ordinary skill in the art. Such lenses are commercially available and include, but are not limited to, CRYSTALENS®, REZOOM®, and ACRYSOF RESTOR®.

In all these embodiments, the visual axis must be known so that it can coincide with the center of a device (e.g., for a corneal inlay) or with the center of ablation (e.g., in PRK or LASIK procedures). Inaccurate centration, also referred to as decentration, creates optical problems of alignment when the multiple optical elements in the eye (cornea, lens, retina) must be aligned on top of each other.

In one embodiment, the image is projected or marked on a lens in the visual pathway, e.g., FIG. 1. The lens may be an intraocular lens inserted in the eye, or the lens may be external to the eye (e.g., glasses worn by a user), or the lens may be on a device such as a scope. The image permits centration of all optical elements. In this embodiment no treatment is desired, but accurate visual alignment is desired. In one embodiment, the individual is participating in a sport or activity requiring visual alignment, for example, photography, hunting, golfing, billiards, archery, darts, etc., and can use the image to center his/her visual axis in alignment with an object such as a subject, target, ball, etc. In one embodiment, the individual is using a weapon requiring visual alignment (e.g., rifle, gun, etc.) and can center his/her visual axis in alignment with a human or non-human target. In this embodiment, use may be in simulated combat for training purposes, in actual combat for military purposes, in a national security situation, for example, a sharpshooter sighting a highjacker, a paratrooper attempting to land at a particular target, etc. The image may be placed on devices including, but not limited to, glasses, binoculars, telescopes, weapon scopes, surveying equipment, computer-controlled optics (e.g., surgical instrument, space exploration equipment (e.g., Mars Rovers, Mars Polar Lander)), drills, underwater cameras, etc. In one embodiment, the individual has an occupation requiring visual alignment, such as a soldier, craftsperson, surgeon, technician, astronaut, photographer, etc. It may assist individuals in the military, participating in activities, participating in sports, etc., to recognize landscape relief such as hills, curves, troughs, etc.

Other variations or embodiments of the method and device to assess and use centration of an individual's visual axis will also be apparent to one of ordinary skill in the art from the description.

Evaluation of Retinal and/or Foveal Function

The time interval that photoreceptors take to recover, after they have been stimulated by a set pulse of light energy (i.e., bleached) until they are capable of perceiving a second pulse of the same or weaker light energy (i.e., recovered or non-bleached), is compared to this time interval in a healthy retina to evaluate retinal function and response.

The retina is located at the back of the eye. It contains numerous photoreceptors that, upon stimulation by light arriving in the eye, initiate protein-mediated changes. Specifically, in the presence of light, the protein retinal undergoes a conformation change and, as a result, generates electrical nerve impulses. These electrical impulses travel to the brain, via the optic nerve, depolarizing ganglion cells.

The two major types of photoreceptors are cones and rods. Cones permit central vision and color vision in bright light. Cones are limited to an area of the retina termed the macula, particularly the centermost portion of the macula termed the fovea. The fovea is the area of the retina that is responsible for sharp vision due to its high concentration of cones.

Rods permit peripheral vision and vision in dim light. Approximately 120 million rods are located throughout the retina, and are more common that the 6-7 million cones. Rods are exquisitely sensitive to light, much more so than cones. When bleached with light, however, rods recover much more slowly than cones. Under normal conditions, cone pigments recover within 7 seconds to 15 seconds of bleaching, while rod pigments require more than 8 min to 12 min to recover. Thus, fatigue can be induced in a dark-adapted retina (rod conditions) much more quickly than in a light adapted retina (cone conditions). The cone response can also be eliminated, if needed, by very low levels of light or short wavelengths of light. Light adaptation or 30 Hz rapid flickering will eliminate most of the rod function. In general, optimal vision results when the incoming light rays in the visual axis are accurately centered on the fovea.

An individual who is predisposed to or diagnosed with retinal disease, or an individual being screened for retinal disease, has an improved likelihood of halting the progression of the disease, treating the disease, and/or prolonging vision, if the disease is diagnosed early so that appropriate therapy may commence. Early treatment of retinal diseases shows favorable outcomes. Examples of such diseases include, but are not limited to, retinitis pigmentosa, inherited retinal degenerative diseases, diabetic retinopathy, macular degeneration, macular edema, retinoschisis, hypertensive retinopathy, idiopathic subretinal neovascularization, peripapillary neovascularizations, Best disease, cone-rod dystrophy, viral retinal disease, optic nerve demyelinating diseases, chloroquine toxicity, Timoxifin toxicity, other systemic medication toxicities, central serous choroidopathy, multiple sclerosis, autoimmune diseases of the retina optic nerve, optic nerve pit, coloboma, tumors of the optic nerve or brain, vascular malformations and anomalies, head trauma, etc. An individual may be exposed to substances that affect retinal function. Examples include, but are not limited to, methyl alcohol and carbon monoxide and organic solvent vapors.

Several retinal evaluation systems are available. As one example, multifocal electroretinography (ERG) (Electro-Diagnostic Imaging Inc.) evaluation is in contrast to single mass ERG response from the entire retina. However, this system represents a static evaluation of the electrical function of the retina. As another example, an individual may self-evaluate his/her vision when viewing an Amster grid, which is a quadratic image of intersecting horizontal and vertical lines with a central dot. The individual is directed to look at the dot with one eye, with the other eye covered. An individual with a normal visual field sees an intact Amster grid while an individual with an abnormal visual field, or visual field changes, sees a distorted Amster grid with wavy and/or missing lines; this individual does not see the center but sees an area adjacent to the center. The area seen depends on how much visual acuity has changed or has been lost.

The inventive device and method may be used in various embodiments. One embodiment may be used to objectively evaluate retinal function. This embodiment evaluates retinal function by quantitating the time it takes for the retina to recover after it has been subjected to a light pulse or stimulus (bleached). One embodiment may be used to map, verify, document, etc. the precise location of light stimulation in the retina. One embodiment may be used to subjectively evaluate a patient's central visual field. This embodiment may be used by a medical professional, or by a patient to self-evaluate his/her central visual field. This embodiment may be used to precisely locate a particular area of damage or disease. Any of these embodiments may be used to evaluate overall retinal health, and/or provide information on retinal disease diagnosis, progression, effect of therapy, need for additional and/or invasive therapy, etc.

A retinoscope, fundus camera, computerized monitor, or other instrument may be used to provide the light source.

Incoming light, arriving at the fovea, must be sent along an axis, termed the visual axis. When an individual views two sources of light that are static, that is, not moving, an individual can subjectively distinguish them in his/her visual field only if the two sources are separated by some distance. When the two sources of light are not static, but when they move in the same direction, the separation that the individual subjectively perceives depends on (a) the strength of the light source; (b) the speed of each light source or ray traveling in the same direction, (c) the separation of the two light sources or rays from each other (distance), and (d) the function (health) of the photoreceptors in the retina.

When the incoming light is moving along the outermost periphery of an imaginary circle, in a dark room, in a dark adapted state, or with use of a very weak light (rod function test, Fricker and Sanders, Rod Function Evaluation by the Use of Synchronous Detector Techniques for Electroretinographic Analysis, *Investigative Opthalmology and Visual Science*, 10 (1971) 650-663), it is seen by an individual as leaving a "tail" in its path along the circle. If the "tail" is sufficiently long, it is seen by an individual as making a full circle, that is, the "tail" encompasses the complete circle) (360°) from the starting point and back to the starting point. The test can also be performed in lighted adapted conditions by elimination rod responses (cone function test). The extent of the tail that the individual sees depends on (a) the strength of the light source, regardless of what wavelength is selected (the stronger the light source, the longer the tail), (b) the speed (distance divided by time) that the light is moving, (c) the separation of the two light sources or rays from each other (distance), and (d) the function (health) of the photoreceptors in the retina. At a certain speed, an individual viewing the tail can perceive almost a complete circle.

The incoming light, at the desired wavelength and moving along the periphery, can also be pulsed at one or more desired frequencies in order to separate rod functions from cone functions.

Figure 3A:
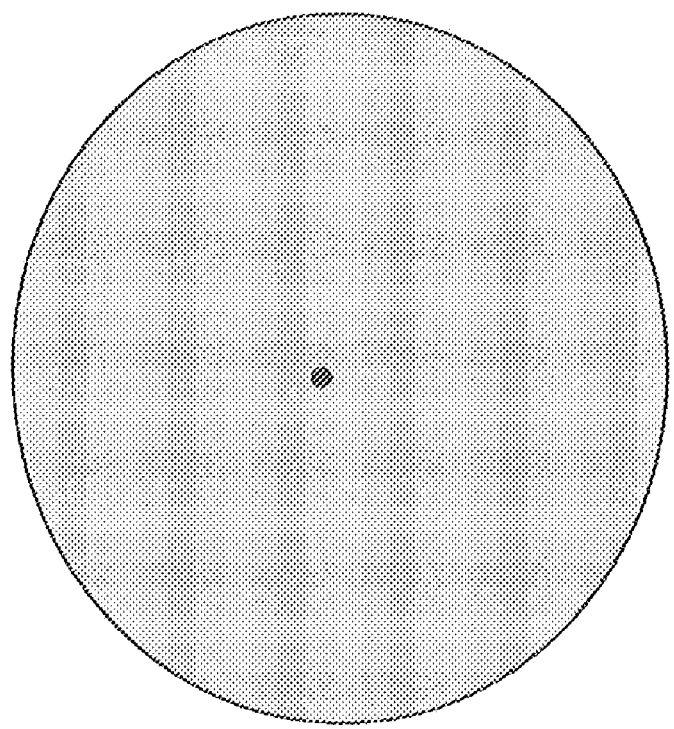
FIGS. 3A, 3B, 3C, 3D, 3E, and 3F shows other embodiments of an image that defines a circle having an area sufficient to identify a focus on its center.
Figure 3B:
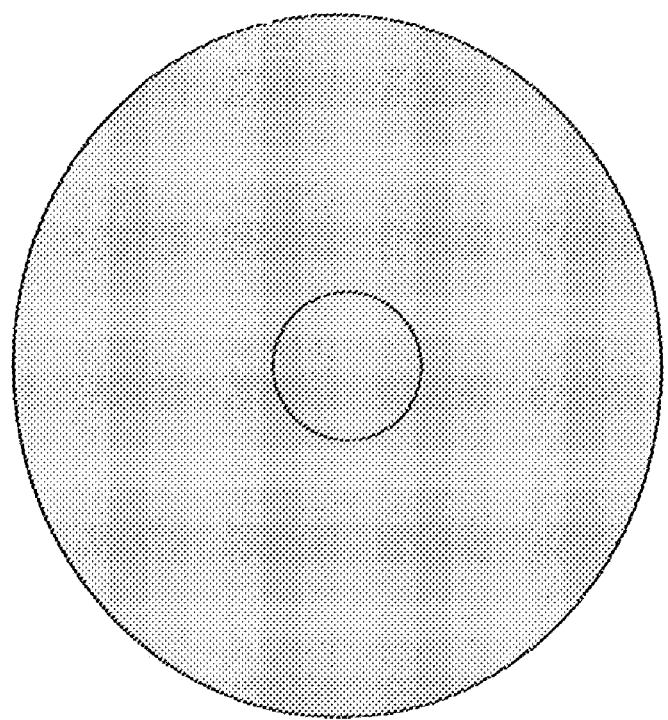
Figure 3C:
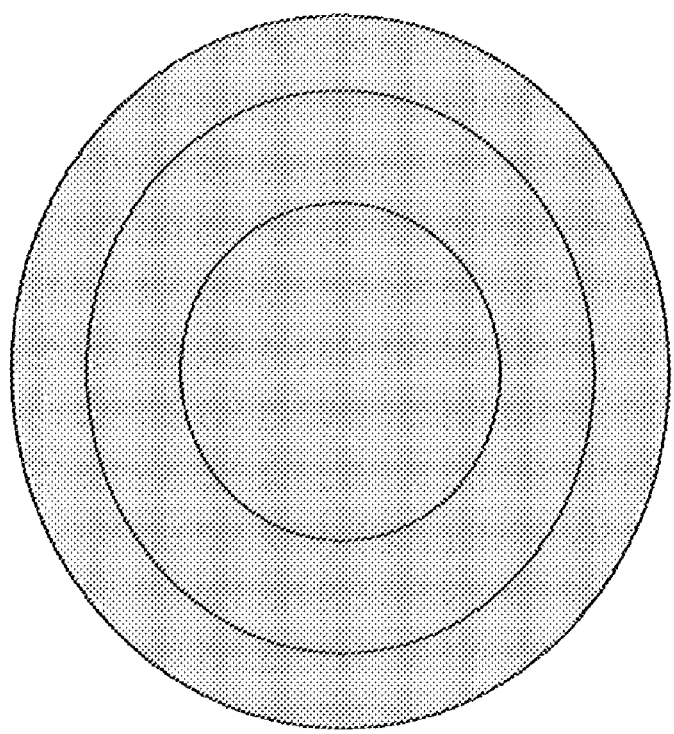
Figure 3D:
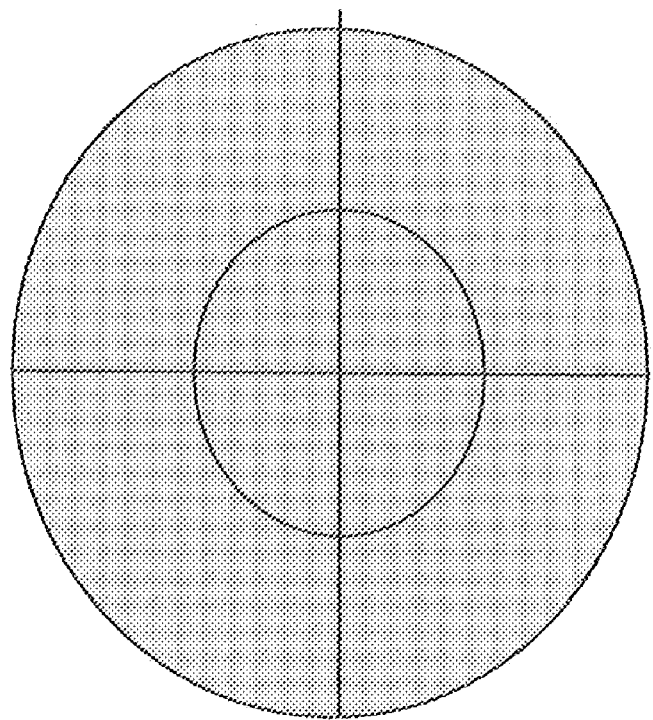
Figure 3E:
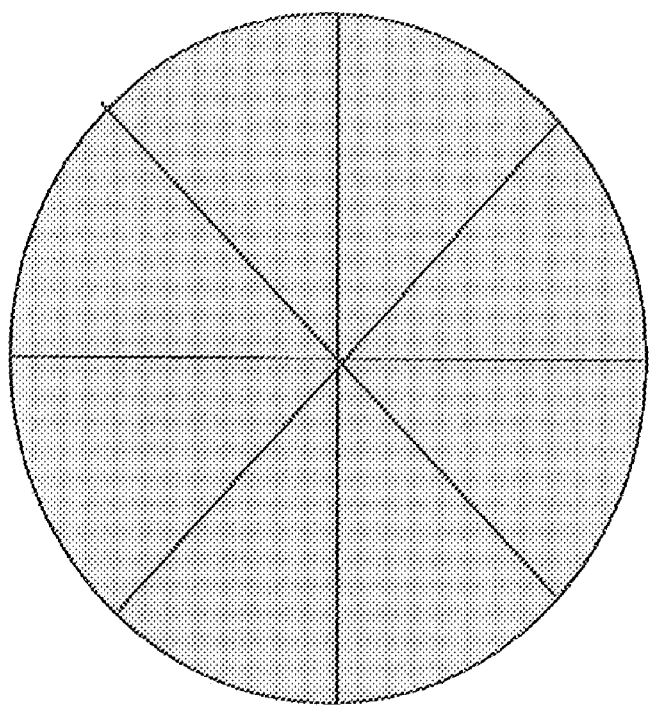
Figure 3F:
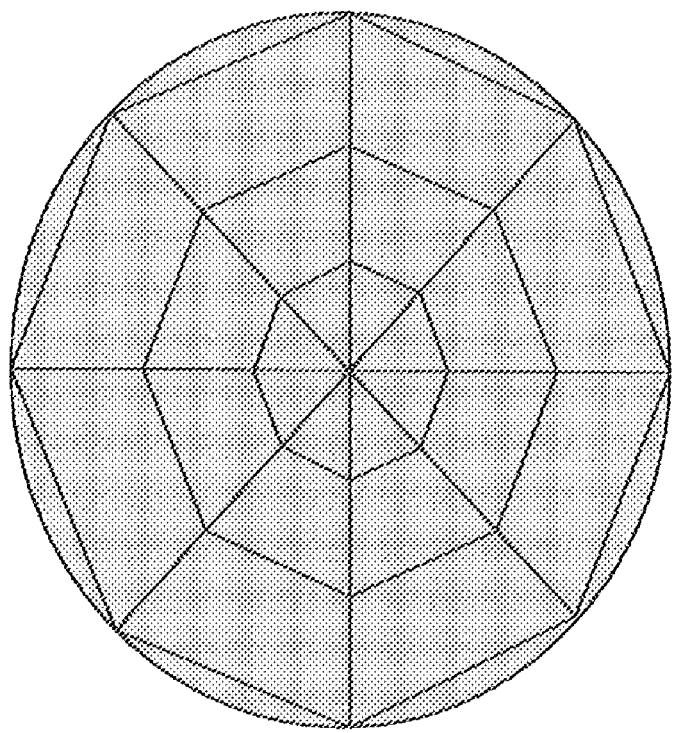

The appearance of the tail depends on the function of the retina in general (rod and cone receptors, e.g., dark adapted state), and the fovea in particular (mostly cone receptors, e.g., light adapted state). In one embodiment, the device and method objectively evaluate retinal function by quantitating the time it takes for the retina to recover to an unbleached state after it has been subjected to a light stimulus (bleached). A patient is instructed to look at the center of an image that defines a circle (circular image), the circle having an area sufficient to identify a focus on its center. The circle may be, but need not be, continuous. In one embodiment, the circular image is at least two concentric circles. In one embodiment, the circular image is one circle. Examples of images are shown in FIG. 1, FIG. 2, FIG. 3A, FIG. 3B, FIG. 3C, FIG. 3D, FIG. 3E, and FIG. 3F. FIG. 1 shows a series of concentric circles. FIG. 2 shows a keratoscope (also known as Placido's disc), a circular image of alternating black and white rings. FIG. 3A shows a single circle with the center indicated as a dot. FIG. 3B shows two concentric circles. FIG. 3C shows three concentric circles. FIG. 3D shows two concentric circles with two axes. FIG. 3E shows a circle with four axes. FIG. 3F shows a circle and octagonal/hexagonal lines to form a net-like or spider web-like structure. Any or all of these images may be used to evaluate retinal function. When the individual looks at the center of such a circular image, the eye recognizes the pattern reflected from the image and self-focuses on the center. This self-focusing on the center occurs even in individuals with a damaged fovea, such as patients with age-related macular degeneration, because the peri-foveal area has a circular representation in the brain.

Figure 4:
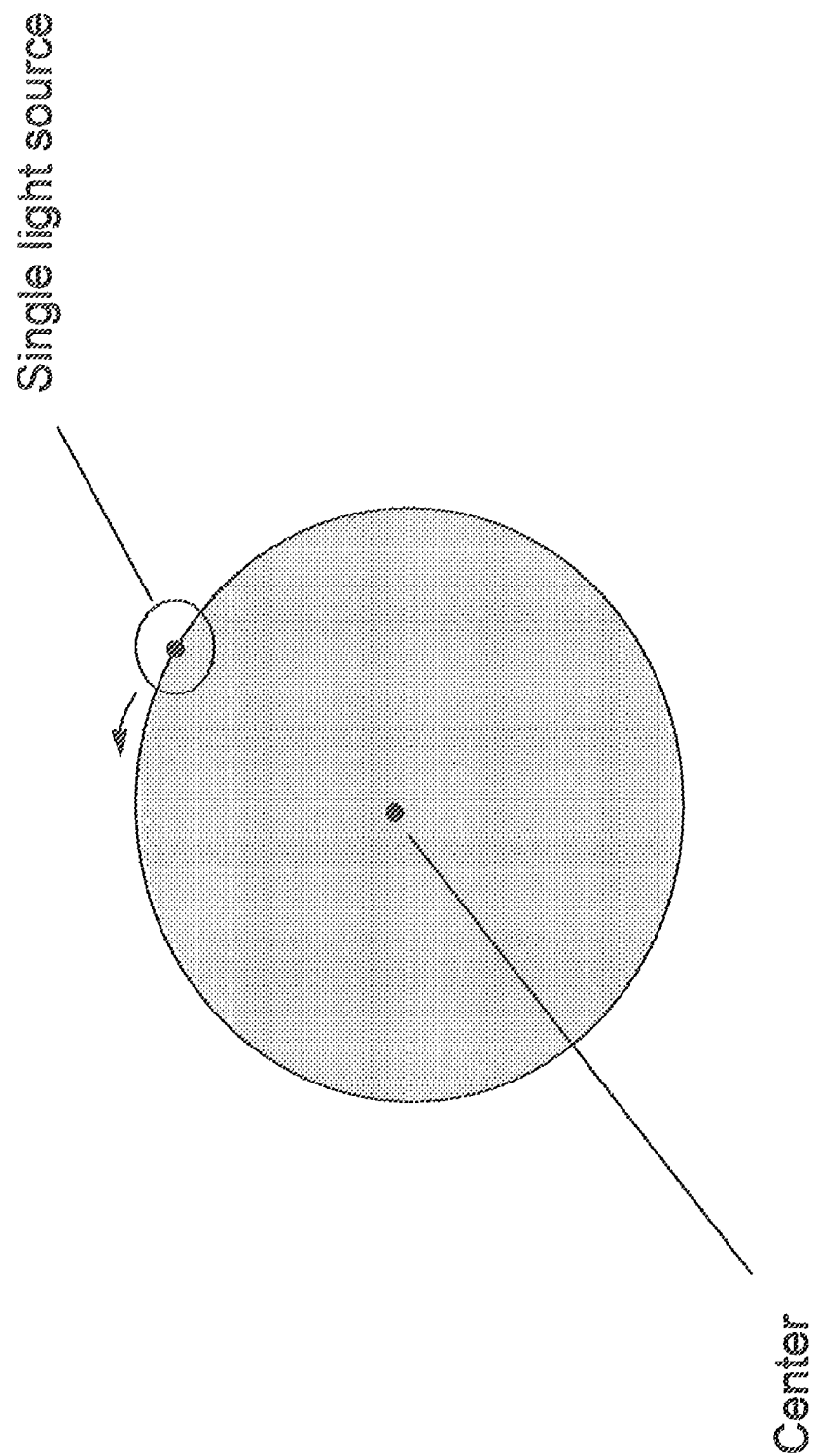
FIG. 4 shows a circular image that contains a single light source at one point on the outermost periphery.

As a non-limiting exemplary illustration of how the images are used to evaluate retinal function and response in this embodiment, a patient is instructed to view the circular image that contains a single light source at one point on the outermost periphery as shown in FIG. 4. The circle can be that of any of the images of FIG. 1, FIG. 2, FIG. 3A, FIG. 3B, FIG. 3C, FIG. 3D, FIG. 3E, or FIG. 3F. The light is set at a selected wavelength, thus the wavelength is known. The light source has been programmed or otherwise made to move at a selected constant speed, thus the speed is known. The light source travels a distance of 360°, either clockwise or counterclockwise, around the outermost periphery, thus the distance is known. Speed is distance divided by time.

The patient is instructed to indicate to the evaluator the earliest time at which he/she sees the moving light on the circle as a complete circle of light, rather than as an incomplete circle of light. This time is the time at which retinal fatigue has occurred, and retinal recovery has been exhausted. FIG. 4. The patient may report this time in any way. For example, he may give an oral response (saying "yes" or "now"), or raise his/her hand with a scribe recording the time interval, or tap a key on a keyboard programmed to record the time interval, etc.

A patient with a healthy retina, viewing any of the images of FIG. 1, FIG. 2, FIG. 3A, FIG. 3B, FIG. 3C, FIG. 3D, FIG. 3E, or FIG. 3F, with the light source moving at a relatively slow constant speed around the outermost periphery, sees the light in a circle that remains open, that is, the circle is never seen as a complete circle at this fixed speed, distance, and wavelength. This is because either retinal fatigue has not occurred, or retinal fatigue has occurred but the healthy retina recovered by the time the moving light source traveled 360° around the circle and reached the original starting point.

A patient with a diseased retina, viewing any of the same images under the same conditions, sees the light in a circle that is closed, that is, the circle is seen as a complete circle at this fixed speed, distance, and wavelength. This is because the photoreceptors in the retina did not recover in time for the moving light source to travel 360° around the circle and reach the original starting point.

Figure 5:
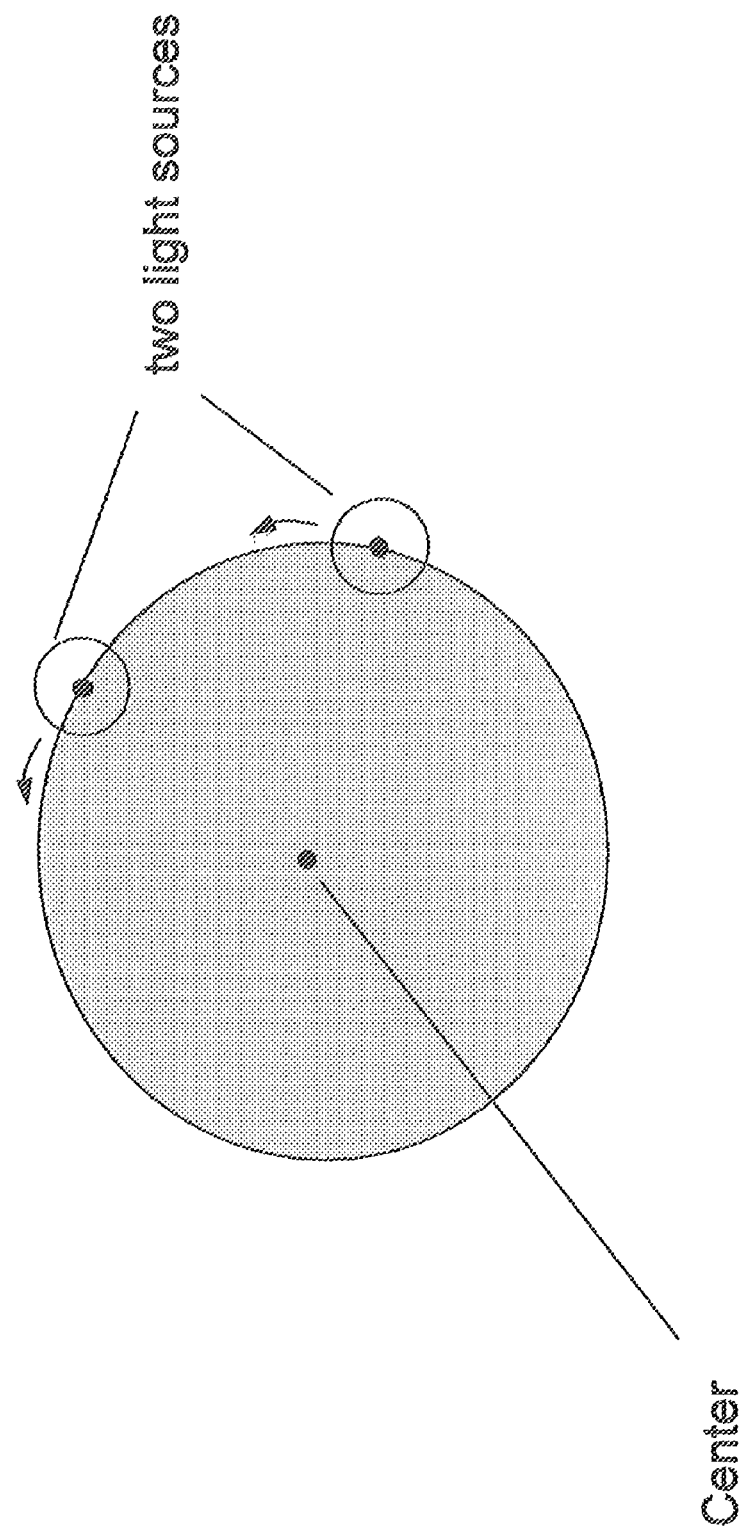
FIG. 5 depicts two light sources spaced in time and distance.

When light travels at such a relatively slow speed, for a given time, it travels over a shorter distance, in comparison to when light travels at a relatively fast speed where, for a given time, it travels over a longer distance. In one embodiment, evaluation occurs as previously described under the same conditions (light or dark adapted), except instead of a single light source there are two light sources as shown in FIG. 5 spaced in time and distance, at set at a distance from a patient that a patient viewing a stationary image sees two distinct light sources. For example, if the peripheral portion of the retina has normal function, but if the fovea function has abnormal function, evaluation of physiological retinal function becomes more difficult. If such a partial abnormality is suspected, or even as a preliminary screening evaluation for all individuals, the inventive device and method may encompass the use of two light sources, versus one light source. Exposure to the first light bleaches the photoreceptors in patients with normal and abnormal retinal function (e.g., foveal function). However, for a patient with abnormal retinal function at the fovea, there is a longer time interval of recovery between the time he/she sees the first light source (arrival of the first light source at the fovea) and the time that he/she sees second light source (arrival of the second light source at the fovea) compared to a patient with normal retinal function.

In this embodiment, the evaluation is performed as previously described for any retinal area. When two light sources move simultaneously at the same speed over a retinal area, the earliest time at which the patient indicates that he/she sees the two light sources as merging into one light source (that is, the earliest time at which the patient cannot distinguishable between the two moving light sources), is the time at which retinal fatigue has occurred, and retinal recovery has been exhausted. FIG. 5.

Speed is the distance traveled in a given time, that is, distance divided by time. In a patient with a diseased retina, the speed at which the light must travel for the patient to perceive a complete circle is slower, in comparison to the speed at which the light must travel for a patient with a healthy retina to perceive a complete circle. This is because a healthy retina recovers faster, e.g., it recovers by the time the moving light reaches its origin (starting point). A diseased retina, however, takes longer to recover. By the time the moving light reaches its origin (starting point), the diseased retina still has not yet recovered. This condition, referred to as retinal fatigue, represents the time for recovery of photoreceptors from the excited state back to the normal state under dark or light adaptation. Accurately measuring under similar conditions and comparing this time interval over days, weeks, months, or years of treatment or disease permits evaluation of therapy in the case of on-going treatment, establishes when intervention (therapy initiation, therapy supplementation by e.g., increased doses, additional drug, surgery, etc.) is warranted, or establishes that the disease has progressed or regressed and that, respectively, more or less frequent evaluation is warranted.

If the identical areas and identical stimuli are not replicated with subsequent evaluations, the results obtained will not be useful, e.g., a physician may see improvement where no improvement of the affected area has occurred; a physician may see decreased function and not appreciate the affected area is greater than previously determine; etc. It is difficult, however, to ensure that the same area is indeed being evaluated and the same stimulus if being provided. The best way to repeatedly evaluate the same spot or area in the retina is to be able to uniformly and consistently project the image at different times. This requires that the size of the image is constant and is always located on the same position on the retina, even if the fovea is not functioning. This is provided by the inventive circular images and by having the patient's eye positioned from the external image at a constant distance at all times to provide the image to be projected on the same area of the retina. This is accomplished by creating one or multiple circular images, or by creating a circular motion, around a central area and instructing the patient to focus on the center. Even in patients with a non-functioning retina due to diseases such as age related macular degeneration, they will self-focus on the center of a continuous circular image, even if the center is not visible.

The following example is illustrative only and not limiting; e.g., the times are relative only and may vary depending upon particular experimental conditions.

The desired circular image is selected and the light source(s) is/are programmed or otherwise set up to move around the outermost periphery in either a clockwise or counterclockwise direction at a set speed and distance. The slower the speed, the more sensitive the evaluation will be because even a patient with some retinal damage may still report seeing an open circle if the light speed is sufficiently slow. The distance the light has traveled for a 360° path (from the starting point, around the outermost periphery of the circle, and back to the starting point) is noted on a given circle. Assuming an average distance for this value in a patient with a healthy retina, a patient with a diseased retina would report seeing a closed circle at lower speed (longer time). For example, a patient that is not dark adapted and with a healthy retina, reports seeing a closed circle if the light moves around the outermost periphery of a circle with a distance of 15 mm in about 3 seconds to about 5 seconds or 12 seconds (within the normal recovery of cone pigment) before it reaches its starting origin. A patient with a diseased retina reports seeing a closed circle even if the light moves slower than about 12 seconds to about 30 seconds to 40 seconds or more before it reaches its starting origin.

Patients with a healthy retina, viewing the image at a set distance, will at some point report that they see a closed circle. The set distance of eye to object is determined arbitrarily, but this distance is maintained constant for subsequent examinations. The patient may be corrected for refractive errors so that only retinal function is evaluated. The patient is positioned so that this distance is maintained throughout the evaluation. For example, the patent's head may be positioned in a chin and forehead rest.

At this set distance, a patient with a healthy retina is evaluated and the time is noted when the patient reports seeing a circle that is closed. A sufficient number of patients with healthy retinas are evaluated such that the mean and standard deviation can be calculated, e.g., at $p<0.05$ or another probability value. If, for example, the time interval is between about 3 seconds to about 5 seconds for a healthy retina, a patient's reported time less than about 5 seconds is assessed as normal retinal function.

Using the same example, patients with a weak or damaged retina, viewing the image at this set distance, will report that they see a circle that is closed at a slower speed than patients with a healthy retina. A reported time of about 24 seconds is evaluated as borderline abnormal and the evaluation should likely be repeated. A reported time greater than about 30 seconds is evaluated as abnormal retinal function. In one embodiment, the method and device may be used to quantitatively evaluate the extent of decreased function and/or damage in patients with a known retinal condition. In this embodiment, the reported time will be greater than about, e.g., 24 seconds, with longer times indicating a greater extent of decreased function. For example, a reported time of 30 seconds indicates more damage than a reported time of 6 seconds, a reported time of 10 seconds indicates more damage than a reported time of 7 seconds, etc. A reported time greater than about 60 seconds indicates severe retinal damage.

The data obtained in a dark adapted state (rod function) differs from the light adapted (cone) state, and can be used accordingly as described for evaluation of retinal function.

Several evaluations may be performed and the mean reported time may be used. For example, three evaluations may be performed, the mean reported time calculated, and the mean used to compare to a reported time from a patient with normal retinal function to evaluate the relative extent of decreased retinal function. This embodiment may also be used to evaluate efficacy of therapy, e.g., after a course of treatment, a decrease in reported time may indicate efficacy of regeneration of photoreceptor function. Thus, the inventive device and method provides a general quantitative estimate of the degree of retinal function. It evaluates the recovery of photoreceptors wherever they are in the retina (i.e., central, peripheral, or both). The embodiments may be simplified for lay use, or may be enhanced for professional use. For example, an enhanced embodiment may include simultaneous routine electrical recording of the retina, which can also provide, during the examination, additional precise information about retinal electrical and/or metabolic function.

The following embodiments may be used as a device and in a method to evaluate foveal function.

As previously described, the fovea is the most sensitive portion of the retina. Optimal vision results when the incoming light rays in the visual axis are accurately centered on the fovea.

A light source moving in a straight line over the fovea leaves an after-image that results in a blinding effect. The afterimage is due to the photoreceptors adapting from being overstimulated and losing sensitivity. This condition, referred to as retinal fatigue, represents the time for recovery of photoreceptors from the excited state back to the normal state. Accurately measuring, and comparing, this time interval over days, weeks, months, or years of treatment or disease permits evaluation of therapy in the case of on-going treatment, establishes when intervention (therapy initiation, therapy supplementation by e.g., increased doses, additional drug, surgery, etc.) is warranted, or establishes that the disease has progressed or regressed and that, respectively, more or less frequent evaluation is warranted.

The persistence of the afterimage depends on the strength of the light source (a stronger source leaves a longer afterimage and results in longer blinding), the speed at which the light is moving, and the function of the retina in general, and the fovea in particular. An afterimage persists on a healthy fovea for a relatively shorter time than an afterimage persists on a damaged and/or diseased fovea. Any abnormal change, e.g., metabolic, toxic, fluid accumulation in and under the retina, inflammation, etc. will influence the physiological function of the macula before anatomical changes become evident.

Figure 6:
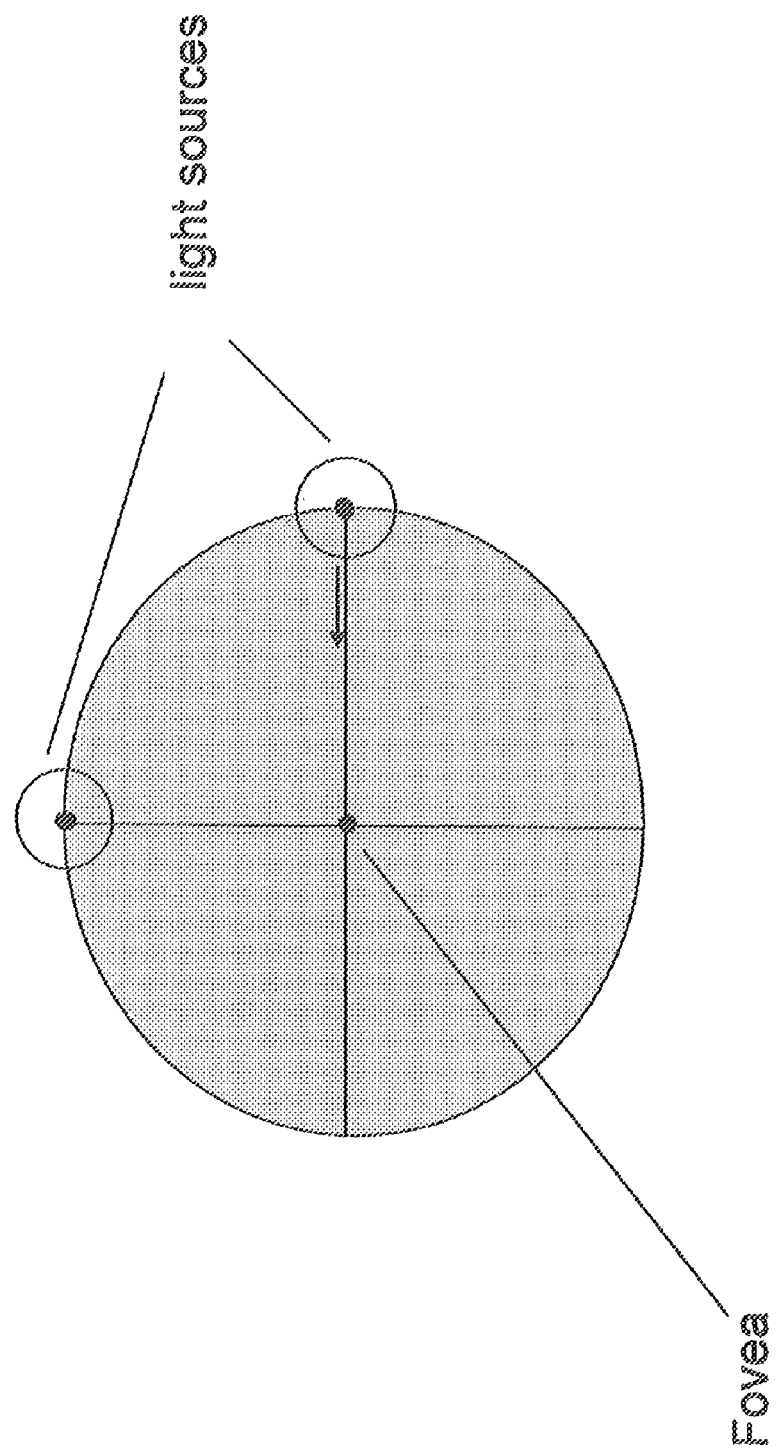
FIG. 6 depicts movement of a light source over at least two possible lines.

To evaluate foveal function, some of the same conditions as previously described for evaluation of retinal function are replicated. That is, a light source is selected at a specific wavelength energy (light or dark state), and is programmed or otherwise made to move, at a selected speed over a selected distance, with the patient viewing a moving light source in a circular image. However, instead of a light source traveling around the outermost periphery of the circular image as for evaluation of retinal function, the light source is programmed or otherwise made to travel along any axis of the circular image, as shown in any of FIG. 1, 3D, 3E, or 3F. In this embodiment, the image shown in any of FIG. 1, 3D, 3E, or 3F is centered so that the center of the circle is centered on the fovea. This is accomplished by having the patient look at the closest circle to the center or the one that he/she can see completely as a circle, so that centration occurs. The patient is then instructed to view the moving light source traveling on a line over the fovea. The motion is repeated at different time intervals. Movement of the light over at least two possible lines is shown in FIG. 6.

Figure 7:
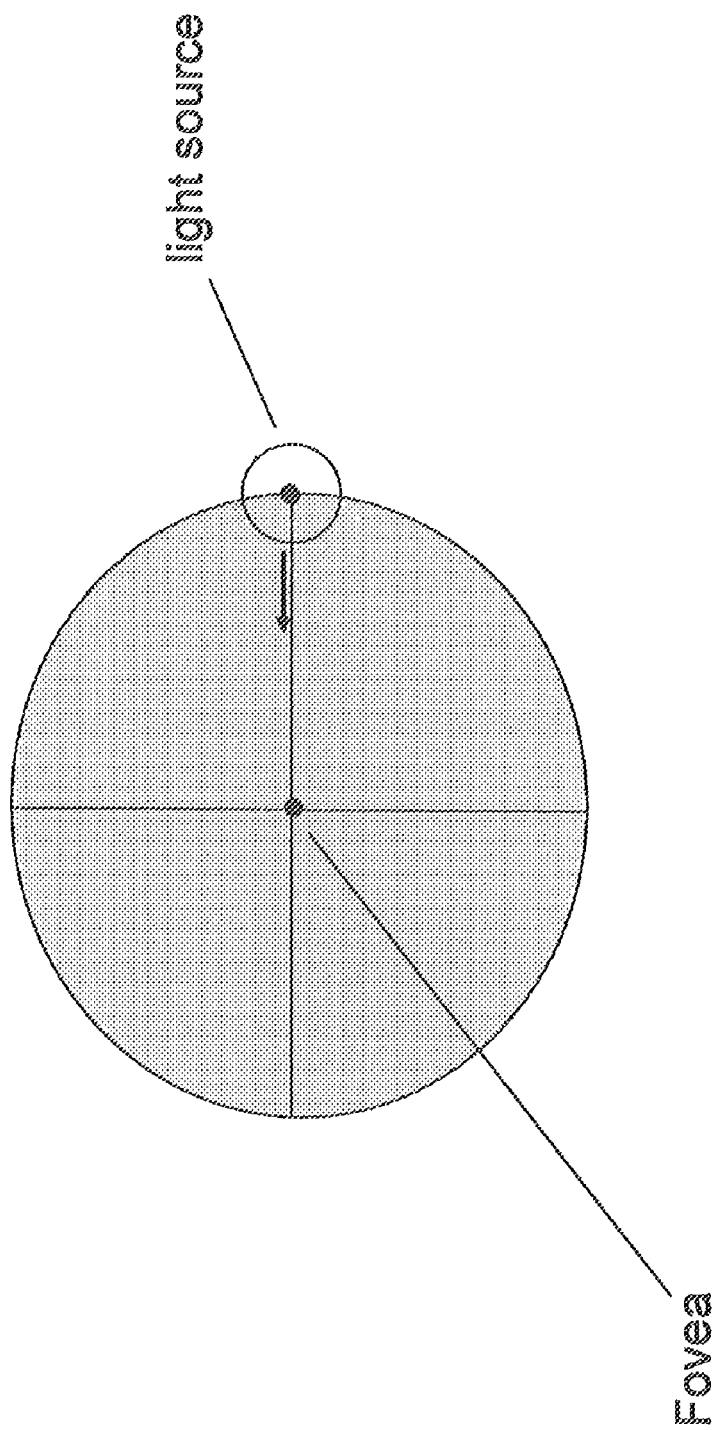
FIG. 7 depicts moving light where the light source is positioned at the right end of the horizontal axis and moves along the axis to the left end.

In a patient with a healthy fovea, at any given light wavelength, the time interval during which the afterimage over the fovea persists is relatively shorter. The patient, viewing the moving light, is instructed to indicate the earliest time at which he/she again sees the light source after experiencing blindness due to the foveal afterimage. The patient response is measured by indicating existence of a new but weaker light pulse. This time is the time at which foveal function is assessed (i.e., the time of recovery of the fovea). The moving light demonstrated in FIG. 7 shows the light source is positioned at the right end of the horizontal axis and moves along the axis to the left end crossing the fovea in the middle. This is in contrast to methods that involve reading a letter or number for a patient response, a process that requires more of a mental or brain involvement.

For these functional evaluations, documenting photoreceptor bleach when the light source should move in front of the patient's eye, a standard computer video/display monitor may or may not be suitable. One alternative is to use a constant light, which does not have the subtle flicker found in most liquid crystal computer displays (LCD), to create on the computer display the line or circle needed for documentation of photoreceptor bleach. Another alternative is to use a LCD with a continuous backlight. Another alternative is to use a display that has a 120 Hz or better refresh rate. In addition, for the functional evaluation, the patient should have a fixation point such as a Placido Disc or slightly lighted circles with intermittent dark circles.

In one embodiment for measuring recovery time in the fovea using a static system, a patient's fovea is stimulated with a strong light pulse, using a pre-selected wavelength (frequency) from a device having a laser or diode source, followed by a very weak light pulse of the same or different frequency, with standardized sequential pulses of low energy at the desired wavelength. When the patient sees or notices the weak pulse, it indicates that at that time, or time/rate (time/rate=number of pulses/second), the recovery has been achieved (recovery time). In this procedure the energy of the initial pulse and subsequent light pulses are accurately determined and can be adjusted; It does not require a patient to "think" or "guess" about a letter or number presented to the patient which could result in misinterpretation of the recovery time results. In addition, the "stimulating" device of this embodiment can have multiple light sources to create a sensation of "background flickering" to bleach rod photoreceptors selectively if needed. This procedure can show not only the cone function, but also create a light wavelength to which the rods are sensitive, by suppressing the cone function.

Another embodiment using the static system measures the recovery time of photoreceptors of the peripheral macula and retina. A Placido Disc, in which the white lines are replaced with lines that are made of liquid crystal that can be illuminated, or a comparable device with intermittent illuminated circles, can be used. A patient's macula or retina is stimulated with a strong pulse of light to bleach a small part or the entire circularly exposed photoreceptors (usually those in the peripheral part of the macula or the peripheral retina) and subsequently stimulated with very weak standardized sequential pulses of low energy, as described above for the fovea. The patient's recognition of the low energy light pulse indicates that recovery has been achieved in that area. Alternatively, only a small part of the Placido Disc, or comparable device, is illuminated and the test performed only in that specific area or any other area. This can be repeated deliberately in the subsequent rings or a part of the rings of the Placido Disc, etc. as desired.

In one embodiment, to measure recovery time of photoreceptors, a moving light source is used. A single light source located in the center of a Placido Disc (moved electronically) projects a light beam in a patient's eye to create the sensation of a lighted line or circle. Using a system similar to that previously described for a static system, instead of projecting the light directly into the eye, one ring or the entire rings of a Placido Disc, is illuminated, e.g., from the back of the Disc. This creates the sensation of a moving light source at a predetermined speed. The after image, when the lights join to produce a circle, indicates the time at which all the photoreceptors in that circular area are completely bleached. Recovery starts when the joined circle begins to become discontinuous. The speed of the light source (distance/time) indicates the recovery rate (how fast or how slow) of the bleached photoreceptors.

In one embodiment, two light sources are at a relatively short distance from each other, e.g., 5° to 10° of arc of separation, on the same Placido Disc. At a certain speed of rotation, the two lights appear as one line. At this time (speed), the photoreceptors between these two light sources have not recovered; they are still in the bleached state. In a diseased retina, the distance (bleached area) between the light sources for a given speed is longer than in a normal retina. Diseased or damaged photoreceptors require a longer time to recover. There is thus a need to accurately measure this recovery for a proper analysis.

In one embodiment, photoreceptor recovery is assessed with a static or moveable light source. A single light source is located in the center of a Placido Disc, which can be moved 360° electromechanically, to project a light beam in a patient's eye at any direction or speed, thus creating the visual sensation of a static or moving beam in the patient's eye. The Disc can also be equipped with a second light source of any wavelength, to be used for various purposes, such as flicker or following the first light's motion at a certain distance (a moving option). The method of checking the photoreceptor recovery using a static beam is as previously described. In the method using the moving beam, there is at least one moving light creating a circular after image at a certain intensity and speed. Alternatively, two light sources are at a relatively short distance from each other, e.g., 10° degree or more arc, on the same circle or line. At a certain speed of rotation or straight line, the two lights appear as one line. At this time, the photoreceptors between the two light sources have not recovered (bleached). In a diseased retina the distance of between the light sources for a given speed is longer than in a normal retina. In this case, the distance between the two light sources can be made smaller or larger. If the motion is a straight line, the length of the line can be determined and the pulse repeated with a different speed until the desired effect, creating an interconnecting line, is achieved.

In a patient with a diseased fovea, at the same given light energy under the same conditions, that is, moving in a linear fashion over the diseased fovea, the time interval during which the afterimage over the fovea persists is relatively longer, in comparison to the time interval an afterimage persists in a patient with a healthy fovea. During this time interval, photoreceptor fatigue has occurred, and photoreceptor recovery has been exhausted as shown in FIG. 8 where light movement can be on either axis.

If the fovea, or any part of the retina, is severely damaged with a complete loss of photoreceptors, the fovea or damaged retina remains dark. The patient never sees the light source from photoreceptors located in this area, indicating that the photoreceptors are non-viable or non-existent in the particular area.

In any of the above embodiments, the image is displayed to the patient for viewing by a means that is not invasive, and that uses a precisely measurable wavelength of light energy. These conditions are in contrast to shining a light beam directly into the eye as a photostress test, which is not easily quantifiable.

Application of Results to Diagnosis/Evaluation

For evaluating either retinal and/or foveal function, the patient results may be compared to a control for diagnosis, and/or the patient results may be compared chronologically for treatment efficacy.

If the results are within the same statistical range as his/her previous test results, this indicates that retinal and/or foveal function is stabilized. If the results are outside the same statistical range as his/her previous test results, this indicates that retinal and/or foveal function has deteriorated. In this case, the physician may take appropriate steps (e.g., increase treatment dose and/or frequency, institute a different or additional treatment, initiate a surgical procedure, etc.).

In one embodiment, a method to assess a specific anatomic area of the retina is described.

By moving a single light source at a predetermined speed over the retina, in either a circle or straight line, one can evaluate the extent of retinal recovery of an area that has been bleached, back to a normal unbleached stated. The bleached area creates a longer after-image from the moving light source than does the unbleached area. The bleached area will respond to a new visual stimulus (e.g., defined light energy) differently than an unbleached area (unbleached because either it has recovered, or because was never bleached at all).

By evaluating different retinal sites, the method measures and/or compares the physiological function between any of the following: two different uncompromised areas of the retina, two different compromised areas of the retina, or one uncompromised and one compromised areas of the retina. This difference can be physiological, that is, due to the physiological function of the foveal, which is the most sensitive area of the retina, and other areas of the retina.

The fovea has a definite anatomic location in the eye, and the method may assess the time interval for recovery of a specific compromised area of the retina and/or fovea. In the method, a single light source is focused at one ocular location peripheral to the fovea (e.g., right or left side of the area thought to be compromised), and then moved laterally across the compromised area and over the fovea to the opposite side (e.g., right to left, or left to right, depending upon the starting location) at a predetermined speed.

A patient with an uncompromised retina and/or fovea sees this single light source, moving at a predetermined speed, as creating an impression of a line.

A patient with a compromised retina and/or fovea, however, experiences prolonged recovery from exposure to the light source and the compromised area remains bleached. When exposed to a single light source moving at this given speed close to the fovea, but turning the light source off as it moves over the fovea, such a patient has the impression that a line still persists, because the fovea is still bleached, until the fovea has recovered. The time at which this patient sees a discontinuous line, versus a continuous line, is the time interval for the fovea to recover.

Besides seeing the continuous line, a patient with a single compromised area of the retina and/or fovea may also see another afterimage. Thus, this patient sees a total of two lights (line and afterimage). A patient with two compromised areas of the retina and/or fovea sees a second afterimage, and thus a total of three lights (line, first afterimage, second afterimage). The use of any of the circular images shown in FIGS. 1-8 can precisely locate the position of the afterimage on the retina using a centration method, as subsequently described. The time interval for recovery of this specific location can be determined by continuing to expose the patient to an image until recovery is noted by the patient's ability to recognize the new stimulus in that area. For example, the exposure can be gradually decreased, starting from a longer interval (e.g., 60 seconds), to shorter intervals (e.g., 20 seconds, 10 seconds, less than 10 seconds, etc.) to determine the recovery time. In one embodiment, the area is exposed to a new light stimulus, such as light with much lower energy at a different time interval. In one embodiment, the image presented contains a number or a letter that the patient under normal conditions is able to recognize.

To assess centration of, and maintain proper centration around, the visual axis, in one embodiment, a patient is instructed to look at the center of an image that defines a circle, the circle having an area sufficient to identify a focus on its center. The circle may be, but need not be, continuous. In one embodiment, the circular image is at least two concentric circles. In one embodiment, the circular image is one circle. Examples of circular images are shown in FIG. 1 and FIG. 2. FIG. 1 is a series of concentric circles. FIG. 2 is a keratocope (also known as Placido's disc), a circular image of alternating black and white rings; when reflected on the cornea, it projects corneal contours that permits a physician to assess corneal surface irregularities and astigmatism, to compute corneal curvature during surgery, and to gather preoperative data in corneal topography assisted LASIK.

When the individual looks at the center of such a circular image, the eye recognizes the pattern reflected from the image and self-focuses on the center. Such centration occurs even in individuals with a damaged fovea, such as patients with age-related macular degeneration, because the perifoveal area has a circular spatial representation in the brain. Thus, by having the patient consistently look at the image, the physician is assured of accurate centration of the visual axis at all times.

The image is displayed by a means that is not invasive and is readily tolerated by a patient. In one embodiment, the image is projected onto the cornea, the lens (if the pupil is dilated), or the retina. The innermost circle is centered around the fovea. This may occur simultaneously with the individual viewing the image. Alternatively, this may occur with the physician viewing the image projected by an instrument on the eye and simultaneously visualizing the retina by a camera. In one embodiment, the image is projected using a device containing software programmed to display and project the image. The device may permit the user to adjust the image size, brightness, intensity, etc. The software may allow measurements to be taken throughout the procedure. In one embodiment, the circles projected may be optically manipulated to become larger or smaller, as needed or desired.

In one embodiment, an image is projected using a computerized Placido disk projecting system as described by Carvalho et al., International Society for Optical Engineering, 2003. As Carvalho reported, its projecting system is attached to the objective lens of a surgical microscope, and the pattern is reflected by a 50% beam splitter attached to the microscope body. The beam splitter contained an adaptor and a CCD monochromatic high resolution camera. A frame grabber is installed on a personal computer and images are digitized at a 480×640 resolution. Algorithms based on image processing techniques are implemented for edge detection of patterns.

In one embodiment, the image is displayed as a hard copy (e.g., on paper) and is positioned within the patient's visual field. In one embodiment, the image is programmed on software and displayed on a computer screen positioned within the patient's visual field. In one embodiment, the image is displayed as a single light or multiple lights on a circle.

In one embodiment, the image is programmed on software and displayed on a computer screen positioned within the patient's visual field. In one embodiment, the image is displayed as a lighted circle. In one embodiment, the image is displayed as a single light on a circular image, such as those shown in any of FIGS. 1-8.

Traditionally, centration is assessed by projecting a beam of light into the eye to define the location of the visual axis. However, this beam of light causes patient discomfort because the patient is instructed to stare at the beam of light for an extended time. Because the patient is rapidly blinded by staring at this beam of light, he/she has a tendency to move the eye, and hence the visual axis, away, thus changing the location of the visual axis. In addition, even a minimal cloudiness in the beam path will cause the eye to move in trying to see it.

Using the inventive method and device, the patient is not exposed to a single beam of light projected into his/her eye (fovea) so there is no discomfort. Patient movement will not occur because the image has a larger area than a single beam of light. Because the patient is instructed to attentively look at the center of circles, the patient automatically centers the fovea in line with the visual axis. The method is used to access centration even on a sub- or non-functional fovea, as occurs in patients with age-related macular degeneration.

In one embodiment to assess centration, the physician marks four areas at the limbus (the edge of the cornea where the cornea meets the sclera) using a dye or an instrument (e.g., as described in U.S. Pat. No. 5,752,967 which is incorporated by reference herein). The physician instructs the patient to attentively focus at the center of either FIG. 1 or FIG. 2. The eye recognizes the pattern reflected from the image and self-focuses on the center of the image. A digitized photograph is taken while the circles are projected on the cornea, defining the relationship between the four peripheral points to the location of the visual axis on the cornea. In one embodiment, the digitized photograph is transferred to a computer. In one embodiment, a test individual self-evaluates his/her central field and potentially marks the distorted area. The central field is the area of the retina (fovea and macular area). The individual is instructed to attentively focus on an image of a continuous circle, or a series of concentric circles, on a screen, or paper, etc. The circles are positioned at a set distance from the patient, standardized by having the patient positioned with chin and forehead rests. Because the image is positioned at a defined distance from the eye, it always creates the same size image over the retina.

In one embodiment, the circles may be illuminated at various points on a given circle (e.g., if paper, the illumination points are holes at a set distance from each other with an illumination source; if digitally projected, the illumination points are electronically set) while the image rotates around its axis at a given speed. In one embodiment, the inventive method and device is used for accurate centration of an intraocular lens that is fixed to the iris or inside the capsular bag, i.e., centration of a multifocal intraocular lens. Examples include centration of phakic lenses, aphakic lenses, pseudophakic lenses, spheric lenses, aspheric lenses, and others known to a person of ordinary skill in the art. Such lenses are commercially available and include, but are not limited to, CRYSTALENS®, REZOOM®, and ACRYSOF RESTOR®.

In all these embodiments, the visual axis must be known so that it can coincide with the center of a device. Inaccurate centration, also referred to as decentration, creates optical problems of alignment when the multiple optical elements in the eye (cornea, lens, retina) must be aligned on top of each other.

Evaluation of Central Visual Field

One embodiment of the inventive method subjectively evaluates a patient's central visual field. This embodiment may be used by a patient to self-evaluate his/her central visual field. This embodiment may be used independent of the patient's functioning macula.

Central visual field may deteriorate in several pathologies affecting vision. One example is age-related macular degeneration. One example is a general retinal disease (e.g., retinitis pigmentosa, diabetic retinopathy, etc.). One example is glaucoma. One example is a neoplastic disease of the eye or brain. One example is a tumor affecting the optic nerve. One example is an inflammatory disease of the eye, retina, or optic nerve. The method and device can be used to determine if visual function is maintained, decreased, or increased in these or other conditions. This embodiment uses the circular image of FIG. 3F, referred to as a "Peyman Net", containing both multiple circles and multiple octagonal/hexagonal lines. For projection over the retina, one needs one or multiple circles that define the visual axis, regardless of the position of the pupil, or function of the macula or fovea. In this embodiment the circular image is static, that is, it does not rotate or move and contains no light source(s) to be viewed. When the individual looks at the center of such a circular image, the eye recognizes the pattern reflected from the image and self-focuses on the center. This self-focusing on the center occurs even in individuals with a damaged fovea, such as patients with age-related macular degeneration, because the peri-foveal area has a circular spatial representation in the brain. Thus, viewing the circular image permits precise centration, which occurs regardless of the condition of the retina, that is, even patients with a diseased retina and/or fovea can be evaluated using this embodiment. By having the image of FIG. 3F placed a known or set distance from the cornea, the net-like configuration permits precise localization or mapping of the specific location of an area to be evaluated.

A physician can evaluate, or a patient can self-evaluate, central visual field by looking at the image. In one embodiment, the patient is fully corrected for refractive errors with lenses. The device is maintained at the same distance from the eye using a chin rest and forehead support. The individual is instructed to focus on the center of concentric circles that are displayed on any medium, e.g., on a computer screen, on paper, etc. The circles are positioned at a set distance from each other. Because the image is positioned at a defined distance from the eye, it always creates the same size image over the retina. The area may be labeled so that patient results can be reproducibly recorded.

Device

The device may display or project the image, and/or may measure the time interval. The image may be displayed as a hard copy (e.g., on paper), displayed on a screen (e.g., on the device itself, on a laptop screen, on a screen in the physician's office, etc.). The device can measure the time interval for either evaluation of retinal and/or foveal function, and/or can display the image. In one embodiment, the device may use a pre-determined statistical correlation accounting for variability within control and diseased populations, to correlate outcome to deterioration of function within a statistical range. The device may allow results to be compared over time (e.g., days, weeks, months, years) with subsequent measurements of same area under the same conditions (e.g., using the same stimulus). In one embodiment, the device is mounted with or otherwise contains a camera or other type of imaging system to permit photography of the retina and capture of a hard copy or digital image. In one embodiment, the circular image may be illuminated at various points. For example, if the circular image is a hard copy, the illumination points are apertures at a set distance from each other with an illumination source. If the circular image is digitally projected, the illumination points are electronically set. Either the light source may move at a given speed around the outermost periphery, or the circular image may rotate at a given speed around its axis.

In one embodiment, the device contains one circular light source. In one embodiment, the device contains at least two light sources. In either embodiment, the device contains a control for the speed of each light source. In one embodiment, the device is programmed with software, e.g., to control the speed of the light sources, to control the brightness of the light sources, to control the wavelengths of the light sources, to assess the time at which the individual sees two sources, to assess the time at which the individual sees one light source, etc. In one embodiment, the device is hand-held. In one embodiment, the device is portable.

In one embodiment, the device for displaying an image to assess and maintain a visual axis comprises a programmable image of a circle having an area sufficient for a human eye to locate a center of the circle, and software to display a visual axis to a user when the human is directed to look at the center of the circle. The entire image, or a part of the image, is selectively illuminated by a single light or a moving light. A point of the image can create a pulse of light to bleach a specific area of the retina and create an after image. In one embodiment, the center of the image initiates a strong pulse of light, creating an after image initially in the center of the retina, followed sequentially with a predetermined weaker pulse of light.

In one embodiment, an instrument provides the above-described image. In one embodiment, the instrument is a handheld device, e.g., cylindrical or square. In one embodiment, the instrument rests on a patient's forehead at an adjustable distance. In one embodiment, the instrument contains software for recording the test performance and parameters during the test. In one embodiment, the instrument is battery operated, with rechargeable batteries. In one embodiment, the instrument generates two different static or moveable light sources that can be pulsed simultaneously, or can be independently controlled by programmable computer software using a miniaturized electromechanical swivel. The instrument controllably initiates, e.g., by a knob, a pulse of light in the center of the retina, focused using appropriate lenses, and controllably adjusts light intensity, e.g., by a rheostat or computer, followed by sequential, adjustable, weaker pulses, and measures the number of pulses delivered at certain time intervals until pulsing is halted by the user after recognition of the weaker pulse.

In one embodiment, the instrument can be controlled by a computer for all its functions, including displaying the number of pulses (equal time) elapsed before the patient has recognized the weaker second pulse.

In one embodiment of the instrument, the light beam is generated by a diode laser at an energy level below the energy level that can lead to permanent damage to the retina. The light beam is focused in the eye by appropriate lenses contained in a housing. In one embodiment of the instrument, the power of one or more diode lasers, duration of interval between pulses, a single shot, and multiple shots, are controlled by a software program.

In one embodiment, the instrument measures the number of weak pulse shots until the patient halts measurement, e.g., by pressing a knob located on the instrument body, or using a remotely controlled mouse or computer. When the patient halts measurement, it indicates that the patient has recognized the weaker pulse.

In one embodiment, the instrument is independent from the patient's response but is equipped with visible light for stimulation, and with detectors to measure the change in returning light, using any visible or infrared light source, indicating photoreceptor bleaching and recovery time. The instrument displays this time, e.g., on a screen.

The instrument, in any of the described embodiments, can be used with a standard or modified fundus camera for simultaneous observation of the fundus. The instrument can be equipped with a standard optical coherence tomography (OCT) system for simultaneous measurement of retinal thickness.

OTHER EMBODIMENTS

A physician performing a retinal and/or fovea) evaluation may simultaneously or concomitantly photograph the area of the retina being evaluated. For example, a CCD or other camera may be mounted on a free standing device containing the image. The physician can thus document the exact location evaluated in real time using any visible or IR light source.

The photograph can ensure a subsequent evaluation is of the same area as in a previous evaluation.

In one embodiment, the image is projected using a device containing software programmed to display and project the image. In one embodiment, the device may allow the circular image to be optically manipulated to become larger or smaller, as needed or desired. The device may permit the user to adjust the image size, brightness, intensity, etc. The software may document time intervals.

In one embodiment, the image is displayed as a hard copy (e.g., on paper) and is positioned within the patient's visual field. In one embodiment, the image is programmed on software and displayed on a computer screen positioned within the patient's visual field.

In one embodiment, the inventive method and device is used to evaluate retinal and fovea) function regardless of the physiological state of the retina and fovea. Thus, the method and device may be used in patients with a healthy retina and fovea, with a weak retina and fovea, and/or with a damaged retina and fovea (e.g., age related macular degeneration, macular edema, etc.), and permits evaluation whether the retina and/or fovea is healthy, weak, and/or damaged, that is, it permits evaluation of retinal and foveal function.

The method introduces a physiological measurement in evaluating retina and/or foveal function that, over time, can precisely predict retinal and/or foveal function improvement, stabilization, or deterioration. Other variations or embodiments will also be apparent to one of ordinary skill in the art from the description. Thus, the foregoing embodiments are not to be construed as limiting the scope of the following claims.

What is claimed is:

1. A method of simultaneously evaluating a visual field and retinal function in a patient, the method comprising
    a. using an instrument containing a light source to shine a relatively stronger pulse of light on an area of the retina wherein a circular image is projected on the retina and an individual is instructed to look at the center of the circle until the patient indicates lack of seeing the light source thereby indicating bleaching the patient's retinal photoreceptors;
    b. using the instrument to shine a plurality of subsequently weaker pulses of light than in step a on the same area of the retina until the patient indicates seeing the light source thereby measuring recovery of the bleached retinal photoreceptors, and
    c. assessing the time interval between a time the patient indicates seeing the light source as in step a, and a time the patient indicates seeing the light source as in step b, to measure the recovery of the bleached retinal photoreceptors as the patient's photoreceptor recovery thereby indicating the patient's photoreceptor health compared to photoreceptor health of a normal individual.

2. The method of claim 1 wherein the instrument is a retinoscope, fundus camera, or computerized monitor.

3. The method of claim 1 wherein the instrument is hand-held.

4. The method of claim 1 wherein the instrument is monocular.

5. The method of claim 1 wherein the instrument is binocular.

6. A method of simultaneously evaluating a visual field and retinal function in a patient, the method comprising
    instructing the patient to look at the center of a target comprising a projected image of circular concentric rings to fixate the patient's vision on the target,
    mapping the visual field and retinal function using a static or moveable light source, and
    recording a recovery time of at least one retinal area by stimulating the retinal area with subsequent weak pulses of light relative to the mapping light source until the weak pulses of light are recognized by the patient.

7. The method of claim 6 wherein the area is a central retinal area, peripheral retinal area, and/or fovea.

* * * * *